United States Patent [19]
Ueda et al.

[11] Patent Number: 5,962,454
[45] Date of Patent: Oct. 5, 1999

[54] NEOVASCULARIZATION INHIBITOR

[75] Inventors: Fusao Ueda, Shiga; Fumitaka Katoh, Osaka, both of Japan

[73] Assignee: Nippon Shinyaku Co., Ltd., Kyoto, Japan

[21] Appl. No.: 08/945,492

[22] PCT Filed: Apr. 19, 1996

[86] PCT No.: PCT/JP96/01069

§ 371 Date: Oct. 20, 1997

§ 102(e) Date: Oct. 20, 1997

[87] PCT Pub. No.: WO96/32945

PCT Pub. Date: Oct. 24, 1996

[30] Foreign Application Priority Data

Apr. 20, 1995 [JP] Japan ........................................ 7/94777

[51] Int. Cl.[6] .................................................. A61K 31/53
[52] U.S. Cl. .............................................................. 514/245
[58] Field of Search ............................................. 514/245

[56] References Cited

FOREIGN PATENT DOCUMENTS

| 57-35587 | 2/1982 | Japan . |
| 58-55423 | 4/1983 | Japan . |
| 59-104320 | 6/1984 | Japan . |
| 2-510927 | 7/1991 | Japan . |
| 3-503459 | 2/1992 | Japan . |
| 4-295427 | 10/1992 | Japan . |
| 4-501474 | 1/1993 | Japan . |
| WO96/04914 | 2/1996 | WIPO . |

OTHER PUBLICATIONS

FEBS, vol. 322, No. 2, 155–158 Irsogladine is a potent inhibitor of angogenesis–Yasufumi Sato et al. (1989).

*Primary Examiner*—Raymond Henley, III
*Attorney, Agent, or Firm*—Graham & James LLP

[57] ABSTRACT

The invention relates to a neovascularization inhibitor composition comprising a compound of the following general formula [I] or a salt thereof, or a solvate thereof, as an active ingredient,

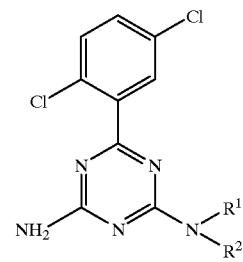

[1]

wherein $R^1$ represents hydrogen, optionally substituted alkyl, aralkyl, arylalkenyl, or aryl; $R^2$ represents optionally substituted alkyl, aralkyl, arylalkenyl, or aryl; or $R^1$ and $R^2$ conjoinedly and taken together with the adjacent N atom, i.e. in the form of $NR^1R^2$, represent a 4- through 8-membered cyclic amino group optionally containing nitrogen, oxygen, or sulfur as a ring member in addition to said N atom and optionally being further substituted.

21 Claims, No Drawings

NEOVASCULARIZATION INHIBITOR

This application is a 371 of PCT/JP96/01069 filed Apr. 19, 1996.

TECHNICAL FIELD

The present invention relates to a neovascularization inhibitor composition.

BACKGROUND ART

The blood vessels, together with the heart and the lymph vessels, constitute a vasculature which is indispensable for sustained metabolism of tissues and, hence, functional homeostasis of an organism. The chief constituent cells of a blood vessel are endothelial cells and smooth muscle cells. Proliferation of endothelial cells in the established vascular system is usually observed in the neovascularization process giving rise to a new network of capillary blood vessels chiefly from venules and the repair process following exfoliation of vascular endothelial cells. As it has recently been made clear that neovascularization is closely involved in pathology of growth of solid tumors, arteriosclerosis, hyperplasia of panni in rheumatoid arthritis, ophthalmic diseases such as diabetic proliferative retinopathy, psoriasis vulgaris, etc., there is a mounting interest in neovascularization.

The mechanism of neovascularization in cancers, rheumatoid arthritis, diabetic retinopathy, etc. is known to begin with a disruption of extracellular matrix which triggers migration of endothelial cells to form a tube which, in turn, is followed by the migration and proliferation of vascular smooth muscle cells around the tube to complete a new blood vessel.

Several compounds (e.g. D-penicillamine, heparin, 15-deoxyspergaulin, eponemycin AGM-1470, tecogalan sodium (DS-4152), herbimycin A, and interferon-alpha) are known to inhibit neovascularization. Those compounds are either biological component-related substances or substances of the natural origin and, therefore, the source of their supply is too limited for practical utilization.

The antitumor agent irsogladine maleate [2,4-diamino-6-(2,5-dichlorophenyl)-1,3,5-triazine maleate], which is structurally close to the compound of the invention, reportedly inhibits neovascularization (FEBS, 322(2), 155–158, 1993). However, the 2-amino-4-substituted amino-6-(2,5-dichlorophenyl)-1,3,5-triazine derivative which is theoretically available upon substitution of one of the amino groups by alkyl, aralkyl, arylalkenyl, or aryl is not known to have neovascularization inhibitory activity.

Meanwhile, the inventors of the present invention previously discovered that the 2-amino-4-substituted amino-6-(2, 5-dichlorophenyl)-1,3,5-triazine derivative has antihepatitis activity and is useful as a therapeutic agent for hepatitis and already filed a patent application (WO 96/04914).

DISCLOSURE OF INVENTION

The object of the present invention is to provide an excellent medicine with low toxicity which is effective in inhibiting neovascularization.

The inventors of the present invention found that the compound of the following formula [I] has remarkably high neovascularization inhibitory activity with extremely low toxicity and have completed the present invention.

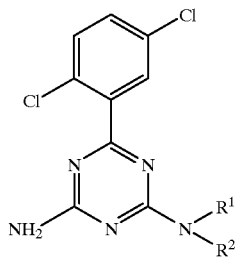

[I]

wherein $R^1$ represents hydrogen, optionally substituted alkyl, aralkyl, arylalkenyl, or aryl; $R^2$ represents optionally substituted alkyl, aralkyl, arylalkenyl, or aryl; or $R^1$ and $R^2$ conjoinedly and taken together with the adjacent N atom, i.e. in the form of $NR^1R^2$, represent a 4- through 8-membered cyclic amino group optionally containing nitrogen, oxygen, or sulfur as a ring member in addition to said N atom and being further substituted.

The present invention, therefore, is directed to a neovascularization inhibitor composition comprising a compound of the above formula [I] or a salt thereof, or a solvate thereof, as an active ingredient.

The present invention is predicated on the finding that the 2-amino-4-substituted amino-6-(2,5-dichlorophenyl-1,3,5-triazine derivative, which has antihepatitis activity as mentioned above, additionally has neovascularization inhibitory activity which is quite unrelated to the first-mentioned activity.

As demonstrated in the experimental examples presented hereinafter, the compound of the invention has by far higher neovascularization inhibitory activity than irsogladine maleate.

The present invention is now described in further detail.

The "alkyl" mentioned for $R^1$ and $R^2$ includes straight-chain or branched alkyl groups of 1–10 carbon atoms, such as methyl, ethyl, n-propyl, isopropyl, n-butyl, isobutyl, sec-butyl, tert-butyl, n-pentyl, isopentyl, n-hexyl, isohexyl, n-heptyl, isoheptyl, n-octyl, isooctyl, n-nonyl, isononyl, n-decyl, and isodecyl. Preferred are $C_{1-4}$ alkyl groups. Such alkyl groups may each be substituted by one, two or three substituents, whether similar or dissimilar, as selected from the group consisting of hydroxy, alkoxy, amino, monoalkylamino, dialkylamino, arylamino, cyclic amino, carboxy, carbamoyl, aryloxy, and acyloxy. The alkoxy mentioned above includes straight-chain and branched alkoxy groups of 1 to 4 carbon atoms, such as methoxy, ethoxy, n-propoxy, isopropoxy, n-butoxy, isobutoxy, sec-butoxy, and tert-butoxy. The alkyl of said monoalkyl- or dialkylamino includes straight-chain and branched alkyl groups of 1–4 carbon atoms, such as methyl, ethyl, n-propyl, isopropyl, n-butyl, isobutyl, sec-butyl, and tert-butyl. The aryl of said arylamino or aryloxy includes aryl groups of 6–13 carbon atoms, such as phenyl, 1-naphthyl, 2-naphthyl, and biphenyl. Particularly preferred is phenyl. Those aryl groups may each be substituted by one or 2–3 similar or dissimilar substituents selected from the group consisting of straight-chain or branched $C_{1-4}$ alkyl (e.g. methyl, ethyl, n-propyl, isopropyl, n-butyl, isobutyl, sec-butyl, tert-butyl) and $C_{1-4}$ alkoxy (e.g. methoxy, ethoxy, n-propoxy, isopropoxy, n-butoxy, isobutoxy, sec-butoxy, tert-butoxy). The cyclic amino as a substituent for said alkyl includes saturated or unsaturated groups such as azetidin-1-yl, pyrrolidin-1-yl, 3-pyrrolin-1-yl, piperidino, hexamethyleneimino, octahydroazocin-1-yl, piperazin-1-yl, homopiperazin-1-yl, morpholino, and thiomorpholino. Particularly preferred are piperidino, piperazin-1-yl, and morpholino. This cyclic amino group may be substituted by $C_{7-14}$ aralkyl such as benzyl, phenethyl, phenylpropyl, phenylbutyl, 1-naphthylmethyl, 2-naphthylmethyl, and diphenylmethyl. The particularly preferred substituent is benzyl. The acyl of said acyloxy includes $C_{1-6}$ alkanoyl (e.g. formyl, acetyl, propionyl, butyryl, valeryl, hexanoyl), $C_{7-10}$ aroyl (e.g. benzoyl), and heterocyclylcarbonyl (e.g. nicotinoyl), among others. Particularly preferred is benzoyl.

The "aralkyl" for $R^1$, $R^2$ includes $C_{7-14}$ aralkyl such as benzyl, phenethyl, phenylpropyl, phenylbutyl, 1-naphthylmethyl, 2-naphthylmethyl, or diphenylmethyl. Particularly preferred is benzyl.

The "arylalkenyl" for $R^1$, $R^2$ includes $C_{8-10}$ arylalkenyl such as styryl, cinnamyl, or 4-phenyl-2-butenyl.

The "aryl" for $R^1$, $R^2$ includes $C_{6-13}$ aryl such as phenyl, 1-naphthyl, 2-naphthyl, or biphenyl. Particularly preferred is phenyl.

The "cyclic amino" for $NR^1R^2$ includes saturated or unsaturated cyclic amino groups. Thus, there may be mentioned azetidin-1-yl, pyrrolidin-1-yl, 3-pyrrolin-1-yl, piperidino, hexamethyleneimino, octahydroazocin-1-yl, piperazin-1-yl, homopiperazin-1-yl, morpholino, thiomorpholino, etc. This cyclic amino may be substituted by one or 2–4 similar or dissimilar substituents selected from the group consisting of hydroxy, oxo, carboxy, alkyl, hydroxyalkyl, aryloxyalkyl, aminoalkyl, alkylsulfonylaminoalkyl, alkylsulfonylamino, alkylsulfonylaralkyl, alkylsulfonyl, aryl, aralkyl, and 2-pyrimidinyl. The alkyl moiety of any such substituent includes straight-chain or branched $C_{1-4}$ alkyl such as methyl, ethyl, n-propyl, isopropyl, n-butyl, isobutyl, sec-butyl, or tert-butyl. The aryl of said substituent groups for said cyclic amino includes $C_{6-12}$ aryl groups such as phenyl, 1-naphthyl, 2-naphthyl, and biphenyl. This aryl may be substituted by one or 2–3 similar or dissimilar substituents selected from the group consisting of straight-chain or branched $C_{1-4}$ alkyl (e.g. methyl, ethyl, n-propyl, isopropyl, n-butyl, isobutyl, sec-butyl, tert-butyl) and $C_{1-4}$ alkoxy (e.g. methoxy, ethoxy, n-propoxy, isopropoxy, n-butoxy, isobutoxy, sec-butoxy, tert-butoxy). The aralkyl includes $C_{7-14}$ aralkyl groups such as benzyl, phenethyl, phenylpropyl, phenylbutyl, 1-naphthylmethyl, 2-naphthylmethyl, and diphenylmethyl. The aryl moiety of this aralkyl may be substituted by one or 2–3 similar or dissimilar substituents selected from the group consisting of straight-chain or branched $C_{1-4}$ alkyl (e.g. methyl, ethyl, n-propyl, isopropyl n-butyl, isobutyl, sec-butyl, tert-butyl) and $C_{1-4}$ alkoxy (e.g. methoxy, ethoxy, n-propoxy, isopropoxy, n-butoxy, isobutoxy, sec-butoxy, tert-butoxy).

Preferably, $R^1$ and $R^2$ each represents $C_{1-4}$ alkyl substituted by one substituent. Particularly preferred is alkyl substituted by hydroxy. Most preferable is hydroxyethyl.

$NR^1R^2$ is preferably a 5- or 6-membered cyclic amino group which is either unsubstituted or substituted by one or 2 similar or dissimilar substituents and more preferably represents pyrrolidin-1-yl, piperidino, or morpholino. Particularly preferred is pyrrolidin-1-yl. The preferred substituent for this cyclic amino is hydroxy or hydroxyalkyl. The hydroxyalkyl is preferably hydroxymethyl.

The compound [I] of the invention may be used in the free form or in the form of a pharmacologically acceptable acid addition salt, such as salts with inorganic acids (e.g. hydrochloride, sulfate, nitrate, phosphate, hydrofluoride, hydrobromide) or salts with organic acids (e.g. acetate, tartrate, lactate, citrate, fumarate, maleate, succinate, methanesulfonate, ethanesulfonate, benzenesulfonate, toluenesulfonate, naphthalenesulfonate, camphorsulfonate). The compound (I) can also be used in the form of a solvate.

The solvate of the compound of the invention includes the hydrate, ethanolate, and other pharmacologically acceptable solvates.

The compound [I] of the invention can be prepared, for example by the following process [WO96/04914].

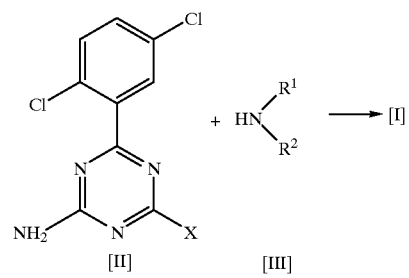

In the above reaction scheme, $R^1$ and $R^2$ are as defined hereinbefore; X represents halogen such as chlorine or bromine.

Thus, [I] can be prepared by reacting a compound [II] with amine [III] in the presence of a base in an inert solvent at 0°–200° C., preferably 25°–100° C. The reaction solvent that can be used includes aprotic polar solvents such as acetonitrile, dimethyl sulfoxide and N,N-dimethylformamide (DMF), ethers such as tetrahydrofuran, dimethoxyethane, diethyl ether and dioxane, glymes such as methylcellosolve and ethylcellosolve, halogenated hydrocarbons such as methylene chloride and chloroform, hydrocarbons such as benzene, toluene and xylene, and mixtures of those solvents. The base that can be used includes inorganic bases such as alkali metal carbonates (e.g. potassium carbonate, sodium carbonate), alkali metal hydrogen carbonates (e.g. potassium hydrogen carbonate, sodium hydrogen carbonate) and alkali metal hydroxides (e.g. potassium hydroxide, sodium hydroxide) and organic bases such as triethylamine and pyridine. In lieu of such a base, the amine ($HNR^1R^2$) may be used in excess.

The reaction time depends on species of the starting compounds, base, and solvent but may range from several minutes to 24 hours.

The molar ratio of amine [III] to compound [II] is generally at least equimolar and preferably 1–1.2 molar. The amount of the base is generally at least equimolar and preferably 1–2 molar equivalents in proportion to [II].

The compound [Ia] of the invention wherein $R^1$ and/or $R^2$ is alkyl substituted by amino or hydroxy in any desired position or the group represented by the formula $NR^1R^2$ is substituted by aminoalkyl, hydroxyalkyl or hydroxy in any desired position or positions can be prepared by the following alternative process.

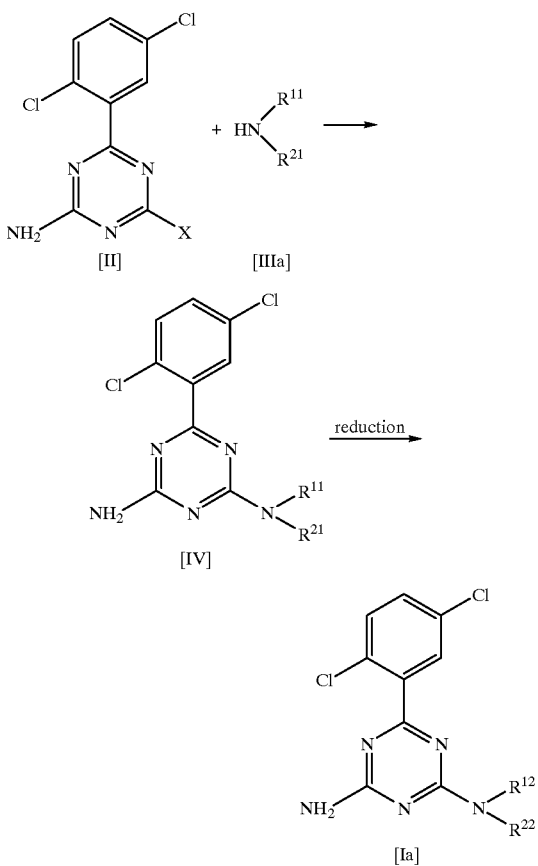

In the above reaction schema, X is as defined hereinbefore. $R^{11}$ and $R^{21}$ each represents an alkyl group substituted by carbamoyl, cyano, alkoxycarbonyl, or oxo in any substitutable position or $NR^{11}RR^{21}$ represents a cyclic amino group substituted by carbamoyl, cyano, alkoxycarbonyl, or oxo in any substitutable position. $R^{12}$ and/or $R^{22}$ represents an alkyl group substituted by amino or hydroxy in the position corresponding to said carbamoyl, cyano, alkoxycarbonyl or oxo in $R^{11}$, $R^{21}$, or $NR^{12}R^{22}$ represents a cyclic amino group substituted by aminoalkyl, hydroxyalkyl, or hydroxy in the position corresponding to said carbamoyl, cyano, alkoxycarbonyl, or oxo in $NR^{11}R^{21}$.

The corresponding amine [IIIa] having carbamoyl, cyano, alkoxycarbonyl, or oxo in an optional position is reacted with compound [II] in the same manner as above to give compound [IV] which is then reduced to provide compound [Ia].

This reduction reaction can be carried out by a per se known method, for example using a metal hydrogen complex compound such as lithium aluminum hydride or sodium borohydride. The compound [Ia] of the invention can be prepared typically by dissolving compound [IV] in 2–100 volumes of an ether solvent, e.g. diethyl ether, tetrahydrofuran, dimethoxyethane or dioxane, and reacting it with 0.25–1.0 mole of lithium aluminum hydride at −50° C. to 30° C. for 0.5–10 hours. When sodium borohydride is employed, the reaction can be carried out in a protoic solvent such as methanol, ethanol or isopropyl alcohol in lieu of said ether solvent in otherwise the same manner as above.

The starting compound [II] can be prepared by the known production technology (JP Kokai S51-70781). Compounds [III] and [IIIa] can be purchased from commercial sources or synthesized starting with commercial compounds.

Some species of the compound of the invention have a asymmetric carbon(s) and may therefore be optically active but such optical isomers and mixtures thereof also fall within the scope of the invention.

Such optically active compounds can be obtained by isolation with a chiral column or by an optical resolution method utilizing their basicity which comprises using an optically active acid (tartaric acid, dibenzoyltartaric acid, mandelic acid, 10-camphorsulfonic acid, etc.). They can also be synthesized starting with optically active compounds [III] or [IIIa] prepared in advance.

The compound [I] of the invention can be changed to salts in the per se known manner. For example, the hydrochloride of compound [I] according to the invention can be provided by dissolving compound [I] in an alcoholic solution of hydrogen chloride.

Among species of compound [I] of the invention, the carboxy-containing compounds can be changed to salts in the per se known manner. The salts may for example be alkali metal salts such as the corresponding sodium salts and potassium salts, and alkaline earth metal salts such as the corresponding calcium salts. For example, the alkali metal salt of compound [I] according to the invention can be obtained by adding preferably one equivalent of sodium hydroxide, potassium hydroxide or the like to carboxy-containing compound [I] in an alcoholic solvent. The alkaline earth metal salt of compound [I] according to the invention can be provided by dissolving the alkali metal salt obtained as above in water, methanol, ethanol, or a mixture thereof and adding one equivalent of calcium chloride or the like.

The solvate (e.g. hydrate, ethanolate) of the compound [I] or salt of the invention also falls within the scope of the invention. The solvate may be obtained, depending on species of compound, by recrystallizing the compound or salt from the corresponding solvent or a suitable mixed solvent containing the corresponding solvent. For example, the hydrate may be obtained by recrystallizing compound [I] of the invention from an aqueous alcohol.

The compound [I] of the invention may assume polymorphism. Such polymorphs also fall within the scope of the invention.

The compound [I] of the invention, thus prepared, can be isolated and purified, as a free base or an acid addition salt, by per se known procedures such as concentration, pH adjustment, redistribution, solvent extraction, crystallization, fractional distillation, and chromatography.

The dosage of the compound in its application as a neovascularization inhibitor, a therapeutic drug for arteriosclerosis, an antitumor agent, a therapeutic drug for Kaposi's sarcoma, a therapeutic drug for diabetic retinopathy, or a therapeutic drug for rheumatoid arthritis is preferably selected with reference to patient factors such as age and body weight, route of administration, nature and severity of disease, and other clinical circumstances. Usually, however, the oral dosage for adult humans, for instance, may range from 0.1 mg to 1 g/patient and preferably from 1 mg to 100 mg/patient as the active ingredient. There are cases in which a higher dosage is needed or a lower dosage is sufficient. The above daily dosage is preferably administered in 2 to 3 divided doses.

The compound of the invention can be administered either as it is or in the form of a pharmaceutical composition containing 0.1%–99.5%, preferably 0.5%–90%, of the compound in a pharmaceutically acceptable nontoxic carrier or vehicle to mammalian animals inclusive of man.

The carrier or vehicle that can be used includes one or more solid, semisolid, or liquid diluents, fillers, or other formulation auxiliaries. The pharmaceutical composition is preferably administered in a unit dosage form. The pharmaceutical composition of the invention can be administered orally, parenterally, locally (e.g. transdermal delivery), or rectally. Of course, the dosage form suited for a selected route of administration should be employed. Oral administration, in particular, is preferred.

Oral administration can be carried out using a solid or liquid unit dosage form such as bulc powders, powders, tablets, dragees, capsules, granules, suspension, solution, syrup, drops or sublingual tablets.

Bulc powders are prepared by comminuting the compound of the invention to a suitable particle size. Powders can be manufactured by blending the so-comminuted compound of the invention with a similarly comminuted pharmaceutical carrier such as, an edible carbohydrate, e.g. starch, mannitol. Where necessary, a flavorant, preservative, dispersant, color, perfume, etc. may be added.

Capsules can be manufactured by filling capsule shells, e.g. gelatin capsule shells, with the above-mentioned bulc powders or powders or the granules prepared as described hereinafter for tablets. Prior to filling, said powders or granules may be formulated with a lubricant or fluidizing agent such as colloidal silica, talc, magnesium stearate, calcium stearate or solid polyethylene glycol. The availability of the drug after ingestion of capsules can be improved by addition of a disintegrator or solubilizer, such as carboxymethylcellulose, carboxymethylcellulose calcium, low-substitution-degree hydroxypropylcellulose, croscarmellose sodium, carboxymethylstarch sodium, calcium carbonate or sodium carbonate.

The fine powders of the compound of the invention may be suspended or dispersed in a vegetable oil, polyethylene glycol, glycerin, or a surfactant and wrapped in gelatin sheets to provide soft capsules. Tablets can be manufactured by preparing a powdery mixture containing an excipient, granulating or slugging the mixture, adding a disintegrator or a lubricant, and compressing the whole mixture into the tabular form. The powdery mixture can be prepared by mixing the appropriately comminuted compound with the above-mentioned diluent or base, optionally with addition of a binder (e.g. carboxymethylcellulose sodium, methylcellulose, hydroxypropylmethylcellulose, gelatin, polyvinylpyrrolidone, polyvinyl alcohol), a dissolution retardant (e.g. paraffin), a reabsorption promoter (e.g. quaternary salts), and an adsorbent (e.g. bentonite, kaolin, dicalcium phosphate, etc.). The powdery mixture can be first wetted with a binder such as a syrup, a starch paste, gum arabic, a cellulose solution, or a polymer solution, stirred to mix, dried, and crushed to give granules. Instead of granulating the powders in this way, it is possible to compress the powders with a tablet machine in the first place and then pulverize the resulting crude-form slugs to provide granules. The granules can be protected from interadhesion by adding a lubricant such as stearic acid, its salt, talc or mineral oil. The lubricated mixture is then compressed. The uncoated tablets thus obtained can be film-coated or sugar-coated.

The compound of the invention can be mixed with a free-flowing inert carrier and directly compressed without resort to the above-mentioned granulation or slugging procedure. Transparent or translucent protective coats such as a hermetic shellac coat as well as sugar or polymer coats and wax glaze coats can also be applied. Other oral compositions, such as a solution, syrup and elixir can also be prepared in unit dosage forms each containing a predetermined amount of the active ingredient. A syrup is prepared by dissolving the compound of the invention in a suitable flavored aqueous medium, and the elixir can be manufactured using a nontoxic alcoholic vehicle. Suspensions can be manufactured by dispersing the compound of the invention in a nontoxic vehicle. Where necessary, a solubilizer or emulsifier (e.g. ethoxylated isostearyl alcohol, polyoxyethylene sorbitol esters), a preservative, a corrigent or flavor (e.g. peppermint oil, saccharin) and others can also be added.

Where necessary, the unit dosage for oral administration can be provided in a microencapsulated form. This kind of preparation may be coated or embedded in a polymer matrix or a wax to insure a prolonged action or sustained release.

For parenteral administration, a liquid unit dosage form for subcutaneous, intramuscular, or intravenous administration, in the form of a solution or a suspension, can be employed. Such unit dosage forms can be provided by suspending or dissolving a predetermined amount of the compound of the invention in a nontoxic liquid vehicle suitable for injection, such as an aqueous or oily medium, and sterilizing the suspension or solution. For isotonizing such injectable preparations, a nontoxic salt or a solution thereof can be added. In addition, a stabilizer, a preservative, and/or an emulsifier can also be concomitantly used.

Rectal administration can be made by using suppositories manufactured by dissolving or suspending the compound of the invention in a low-melting water-soluble or -insoluble solid base such as polyethylene glycol, cacao butter, semi-synthetic fat (e.g. Witepsol™), higher esters (e.g. myristyl palmitate), or a mixture thereof.

The toxicity of the compound of the invention is very low as will be described hereinafter.

The neovascularization inhibitory action of the compound of the invention could be confirmed by the in vitro tube formation test as described below in Experimental Example 1.

As test compounds, the following compounds were used.
- 2-Amino-4-[N,N-bis(2-hydroxyethyl)amino]-6-(2,5-dichlorophenyl)-1,3,5-triazine (compound 1)
- 2-Amino-4-(2,5-dichlorophenyl)-6-(3-hydroxymethyl-1-pyrrolidinyl)-1,3,5-triazine hydrochloride (compound 2)
- 2-Amino-4-(2,5-dichlorophenyl)-6-[(2S,4R)-2-hydroxymethyl-4-hydroxy-1-pyrrolidinyl]-1,3,5-triazine (compound 3)

EXPERIMENTAL EXAMPLE 1

Tube Formation Test

Phenol red-free Medium-199 supplemented with 10% fetal calf serum (FCS) and ECV-304 cells were used as the culture medium and the cells, respectively. EHS sarcoma extract (Matrigel™, Becton Dickinson (MA)) was used as the matrix gel.

The wells in the two middle rows of a 24-well multiplate (Corning 258201) were filled with 300 $\mu$l aliquots of Matrigel, and the gelation was effected under spinning with a centrifugal machine (2,000 rpm, 30 min., 37° C.) (culture by the thick gel method). The culture medium was added to the gel, 1 ml per well, and after 24 hours the medium was renewed and $10^3$ cells/well were seeded. After a further 24 hours, the test drug (1/1,000 in dimethyl sulfoxide) was added. After 1 week of incubation, ethanol fixation and nuclear staining with ethidium bromide were carried out and observation was made under the fluorescent microscope. As the test drugs, compounds 1, 2, and 3 and the reference compound irsogladine maleate were used.

The ECV-304 cells in the untreated control group migrated and proliferated radially (in a star-like fashion) to form a stick-like tube, which then branched to form circles in due course, and as the circles were conjoined to each other, a giant meshwork was formed. Using the colonial morphology on day 2 after commencement of culture as an indicator, the effect of the test drug on tube formation was evaluated. As a result, compound 1 was found to completely inhibit branching at $10^{-5}$ M, compound 2 did so at $10^{-6}$ M, and compound 3 completely inhibited formation of circles at $10^{-7}$ and $10^{-6}$ M. On the other hand, the positive control compound inhibited the formation of circles only at $10^{-5}$ M. Those results indicate that the compound of the invention has considerably higher neovascularization inhibitory activity than the reference compound. Moreover, the colony size at this stage was definitely larger in the untreated group than in the treated groups.

The influence of test compounds on colonial morphology on the gel is shown in Table 1.

TABLE 1

The influence of test compounds on colonial morphology on the gel

| Treatment | | Colonial morphology Number of circles |
|---|---|---|
| Untreated control group | | 1 |
| Test drug groups | | |
| Compound 1 | $10^{-4}$M | 0 |
| | $10^{-5}$M | 0 |
| Reference compound | $10^{-5}$M | 0 |
| Untreated control group | | 5 |
| Test drug groups | | |
| Compound 2 | $10^{-6}$M | 1 |
| | $10^{-7}$M | 3 |
| | $10^{-8}$M | 6 |
| | $10^{-9}$M | 7 |
| Compound 3 | $10^{-6}$M | 0 |
| | $10^{-7}$M | 1 |
| | $10^{-8}$M | 2 |
| | $10^{-9}$M | 6 |
| Reference compound | $10^{-5}$M | 2 |
| | $10^{-6}$M | 5 |
| | $10^{-7}$M | 5 |
| | $10^{-8}$M | 6 |

Morphological evaluation was made after another 3 days. As a result, whereas a tube meshwork was found all over in the untreated control group, only independent local circles at most were observed in the treatment groups, indicating inhibition of tube formation. The results are presented in Table 2. Referring to focal morphology (cell proliferation foci) in the table, the degree of intermeshing was evaluated using the number of circles as an indicator. +++ stands for the thorough integrity of a tube lining structure formed, ++ for the formation of circles, + for the formation of a lumen, and − for inhibition of tube formation.

TABLE 2

Tube formation inhibitory action

| Treatment | | Focal morphology (cell proliferation focus) |
|---|---|---|
| Untreated control group | | +++ |
| Test drug groups | | |
| Compound 1 | $10^{-4}$M | − |
| | $10^{-5}$M | − |
| | $10^{-6}$M | + |
| | $10^{-7}$M | + |
| Compound 3 | $10^{-6}$M | − |
| | $10^{-7}$M | + |
| | $3 \times 10^{-8}$M | + |
| | $10^{-8}$M | + |
| | $3 \times 10^{-9}$M | ++ |
| Untreated control group | | +++ |

TABLE 2-continued

Tube formation inhibitory action

| Treatment | | Focal morphology (cell proliferation focus) |
|---|---|---|
| Test drug groups | | |
| Compound 2 | $10^{-6}$M | − |
| | $10^{-7}$M | ++ |
| Reference compound | $10^{-5}$M | + |
| | $10^{-6}$M | ++ |
| | $10^{-7}$M | +++ |

Compound 2 and 3 inhibited tube formation at $10^{-6}$ M and higher concentrations and compound 1 did so at $10^{-5}$ M and higher concentrations. The mechanism of neovascularization inhibition by the compound of the invention remains to be fully elucidated as yet.

EXPERIMENTAL EXAMPLE 2

Effect on Body Weight Gain

Compound 1 was administered orally to 6-week-old male SD rats (5 animals per group) daily and its effect on body weight gain was evaluated. As a result, compound 1 did not affect body weight gain even at a multiple-dose level of 1000 mg/kg.

TEST EXAMPLE 3

Acute Toxicity (Mice)

The test compound was administered orally in a dose of 1 g/kg or 500 mg/kg to 6-week-old male mice (BALB/c) in fasting state and the incidence of death was monitored for 1 week. The test compound was suspended in 0.5% aqueous methylcellulose solution and administered in a single dose of 500 or 1,000 mg/20 ml/kg. Compound 1 caused no death at 1 g/kg.

Acute Toxicity (Rats)

Rats of either sex (SD strain, 280–360 g) were used in groups of 5. The animals were deprived of food from the previous day (16–18 hours before the experiment) and 1 g/kg of compound 1 was administered orally by gastric gavage. The animals were then monitored for death for 1 week. As a result, no death was found at all.

The toxicity of the compound of the invention is, thus, very low.

BEST MODE OF CARRYING OUT THE INVENTION

The following production and working (formulation) examples are intended to describe the present invention in further detail and should by no means be interpreted as defining the scope of the invention.

PRODUCTION EXAMPLE 1

2-Amino-4-[N,N-bis(2-hydroxyethyl)amino]-6-(2,5-dichlorophenyl)-1,3,5-triazine (Compound 1)

To a mixture of 9.2 g of diethanolamine, 200 ml of N,N-dimethylformamide, and 15 g of anhydrous potassium carbonate was added 20 g of 2-amino-4-chloro-6-(2,5- dichlorophenyl)-1,3,5-triazine with stirring at room temperature and the mixture was further stirred at room temperature for 7 hours. This reaction mixture was diluted with 2 L (liters) of water with stirring and then stirred for 1 hour. The resulting crystals were collected by filtration, rinsed with water, and dried to obtain 24 g of white crystals. Those crystals were recrystallized from methanol, collected by filtration, and dried to give 21 g of the title compound as white crystals.

m.p. 199–200° C.
Elemental analysis ($C_{13}H_{15}Cl_2N_5O_2$)
 Calcd. (%): C, 45.36; H, 4.39; N, 20.35
 Found (%): C, 45.58; H, 4.33; N, 20.46

PRODUCTION EXAMPLE 2

2-Amino-4-(2,5-dichlorophenyl)-6-(3-hydroxymethyl-1-pyrrolidinyl)-1,3,5-triazine hydrochloride (Compound 2)

Except that 3-hydroxymethylpyrrolidine was used in lieu of diethanolamine, the reaction procedure of Production Example 1 was otherwise repeated. The compound thus synthesized was dissolved in methanol and while the resulting solution was cooled, 20% HCl/methanol was added. The reaction mixture was then concentrated to about 1/10 of the initial volume and the resulting crystals were collected by filtration to give the title compound as white crystals.

m.p. 241–243° C.
Elemental analysis ($C_{14}H_{15}Cl_2N_5O \cdot HCl$)
 Calcd. (%): C, 44.64; H, 4.28; N, 18.59
 Found (%): C, 44.47; H, 4.34; N, 18.68

PRODUCTION EXAMPLE 3

2-Amino-4-(2,5-dichlorophenyl)-6-[(2S,4R)-2-hydroxymethyl-4-hydroxy-1-pyrrolidinyl]-1,3,5-triazine (Compound 3)

Except that (2S,4R)-4-hydroxy-2-hydroxymethylpyrrolidine was used in lieu of diethanolamine, the procedure of Production Example 1 was otherwise repeated to provide the title compound as white powders.

Elemental analysis ($C_{14}H_{15}Cl_2N_5O_2 \cdot \tfrac{1}{2}EtOH \cdot \tfrac{1}{2}H_2O$)
 Calcd. (%): C, 46.40; H, 4.93; N, 18.04
 Found (%): C, 46.36; H, 4.80; N, 18.24
H-NMR (CDCl$_3$) 67 : 1.7–2.0 (1H, m), 2.1–2.25 (1H, m), 2.67 (1H, bs), 3.4–3.85 (3H, m), 3.95–4.25 (1H, m), 4.35–4.55 (2H, m), 5.53 (2H, d, J=11 Hz), 7.25–7.4 (2H, m), 7.65 (1H, d, J=19 Hz).

PRODUCTION EXAMPLE 4

2-Amino-4-(2,5-dichlorophenyl)-6-[(2S,4R)-(2-hydroxymethyl-4-hydroxy-1-pyrrolidinyl]-1,3,5-triazine (Compound 3/Another Method)

Step 1 Using trans-4-hydroxy-L-proline methyl ester in lieu of diethanolamine, the procedure of Production Example 1 was otherwise repeated to provide 2-amino-4-(2,5-dichlorophenyl)-6-[(2S,4R)-2-methoxycarbonyl-4-hydroxy-1-pyrrolidinyl]-1,3,5-triazine as white powders.

Step 2 To a mixture of 20.9 g of lithium aluminum hydride and 1000 ml of tetrahydrofuran under ice-cooling and stirring, a solution of 100 g of the compound obtained in Step 1 in 300 ml of tetrahydrofuran was added gradually dropwise at 0–5° C. and the reaction was carried out at the same temperature for 3 hours. After the excess lithium aluminum hydride was decomposed, the reaction mixture was filtered and the filtrate was concentrated. The residue was dissolved in ethyl acetate and the solution was washed with water, dried, and concentrated to give a white solid. This solid was recrystallized from ethyl acetate, collected by filtration, and dried to give 74.7 g of the title compound as white crystals.

m.p. 171–173° C.
Elemental analysis ($C_{14}H_{15}Cl_2N_5O_2$)
 Calcd. (%): C, 47.21; H, 4.24; N, 19.66
 Found (%): C, 47.19; H, 4.32; N, 19.55
$[\alpha]^{20}_D = -67.80°$ (MeOH, c=1.053)

FORMULATION EXAMPLE 1

Two (2) grams of compound 1 is weighed and mixed evenly with 70 g of lactose and 30 g of corn starch, followed by addition of 25 ml of 16% hydroxypropylcellulose solution. This mixture is agitation-granulated. After drying, the granules are size-selected, mixed with 2 g of magnesium stearate and 2 g of talc, and compressed with a rotary tablet machine to provide tablets.

FORMULA

In 110 mg per tablet,

| | |
|---|---|
| Compound 1 | 2 mg |
| Lactose | 70 mg |
| Corn starch | 30 mg |
| Hydroxypropylcellulose | 4 mg |
| Magnesium stearate | 2 mg |
| Talc | 2 mg |

FORMULATION EXAMPLE 2

Four (4) milligrams of compound 1 is weighed and mixed evenly with 996 mg of lactose to provide pharmaceutical powders.

INDUSTRIAL APPLICABILITY

Compared with the reference compound, the compound of the present invention has by far higher neovascularization inhibitory activity and is a safe compound with a low toxic potential as mentioned above. Therefore, the compound is useful for the treatment and prevention of arteriosclerosis, tumors, Kaposi's sarcoma, diabetic retinopathy, rheumatoid arthritis, and other diseases in mammals inclusive of man.

What is claimed is:
1. A method of effecting neovascular inhibition in humans or animals which comprises the step of administering to said humans or animals a therapeutically effective amount of a compound of the following formula [I] or a salt thereof, or a solvate thereof,

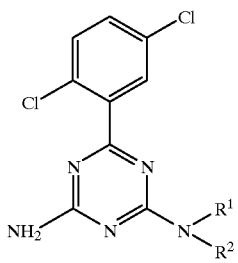

wherein R[1] represents hydrogen, optionally substituted alkyl, aralkyl, arylalkenyl, or aryl; R[2] represents optionally substituted alkyl, aralkyl, arylalkenyl, or aryl; or R[1] and R[2] conjoinedly and taken together with the adjacent N atom, i.e. in the form of NR[1]R[2], represent a 4- through 8-membered cyclic amino group optionally containing nitrogen, oxygen, or sulfur as a ring member in addition to said N atom and optionally being further substituted.

2. The method according to claim 1, wherein R[1] represents (1) hydrogen, (2) alkyl which may be substituted by a substituent selected from the group consisting of hydroxy, alkoxy, amino, monoalkylamino, dialkylamino, arylamino, 4- through 8-membered cyclic amino, carboxy, carbamoyl, aryloxy, and acyloxy, (3) aralkyl, (4) arylalkenyl, or (5) aryl and R[2] represents (1) alkyl which may be substituted by a substituent selected from the group consisting of hydroxy, alkoxy, amino, monoalkylamino, dialkylamino, arylamino, 4- through 8-membered cyclic amino, carboxy, carbamoyl, aryloxy, and acyloxy, (2) aralkyl, (3) arylalkenyl, or (4) aryl.

3. The method according to claim 1, wherein NR[1]R[2] represents a 4- through 8-membered cyclic amino group which may have a substituent(s) selected from the group consisting of hydroxy, oxo, carboxy, alkyl, hydroxyalkyl, aryloxyalkyl, aminoalkyl, alkylsulfonylaminoalkyl, alkylsulfonylamino, alkylsulfonylaralkyl, alkylsulfonyl, aryl, aralkyl, and 2-pyrimidinyl.

4. The method according to claim 1, wherein R[1] and R[2] may be the same or different and each represents hydroxyalkyl or NR[1]R[2] represents pyrrolidin-1-yl, piperidino, or morpholino, which may be substituted.

5. The method according to claim 1, wherein NR[1]R[2] represents pyrrolidin-1-yl which may be substituted by hydroxy, hydroxyalkyl, oxo, alkyl, amino, or aminoalkyl.

6. The method according to claim 1, which comprises administering a compound selected from the group consisting of 2-amino-4-[N, N-bis (2-hyroxyethyl) amino]-6-(2,5-dichlorophenyl)-1,3,5-triazine, 2-amino-4-(2,5-dichlorophenyl)-6-(3-hydroxymethyl-1-pyrrolidinyl)-1,3,5-triazine hydrochloride, and 2-amino-4-(2,5-dichlorophenyl)-6-[(2S,4R)-2-hydroxymethyl-4-hyroxy-1-pyrrolidinyl]-1,3,5-triazine.

7. The method according to claim 1, which comprises administering 2-amino-4-(2,5-dichlorophenyl)-6-[(2S, 4R)-2-hydroxymethyl-4-hydroxyl-1-pyrrolidinyl]-1,3,5-triazine.

8. A method of treating arteriosclerosis in humans or animals which comprising administering to said humans or animals a therapeutically effective amount of a compound of the following formula (I) or a salt thereof, or a solvate thereof:

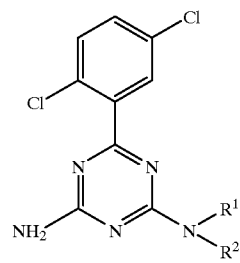

wherein R[1] represents hydrogen, optionally substituted alkyl, aralkyl, arylalkenyl, or aryl; R[2] represents optionally substituted alkyl, aralkyl, arylalkenyl, or aryl; or R[1] and R[2] conjoinedly and taken together with the adjacent N atom, i.e. in the form of NR[1]R[2], represent a 4- through 8-membered cyclic amino group optionally containing nitrogen, oxygen, or sulfur as a ring member in addition to said N atom and optionally being further substituted.

9. A method of treating Kaposi's sarcoma in humans or animals which comprising administering to said humans or animals a therapeutically effective amount of the compound of the following formula (I) or a salt thereof, or a solvate thereof

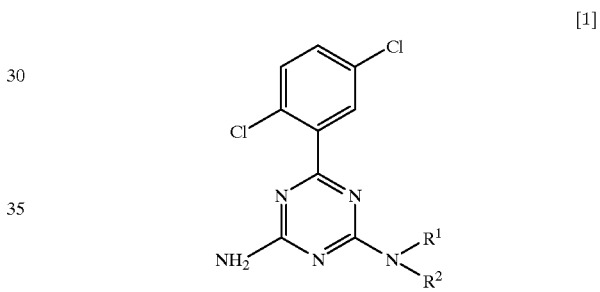

wherein R[1] represents hydrogen, optionally substituted alkyl, aralkyl, arylalkenyl, or aryl; R[2] represents optionally substituted alkyl, aralkyl, arylalkenyl, or aryl; or R[1] and R[2] conjoinedly and taken together with the adjacent N atom, i.e. in the form of NR[1]R[2], represent a 4- through 8-membered cyclic amino group optionally containing nitrogen, oxygen, or sulfur as a ring member in addition to said N atom and optionally being further substituted.

10. A method of treating diabetic retinopathy in humans or animals which comprising administering to said humans or animals a therapeutically effective amount of a compound of the following formula (I) or a salt thereof, or a solvate thereof

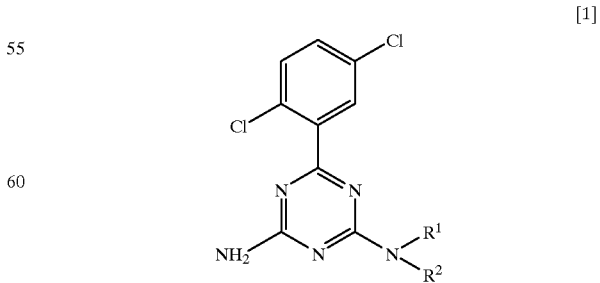

wherein R[1] represents hydrogen, optionally substituted alkyl, aralkyl, arylalkenyl, or aryl; R[2] represents optionally substituted alkyl, aralkyl, arylalkenyl, or aryl; or $R^1$ and $R^2$ conjoinedly and taken together with the adjacent N atom, i.e. in the form of $NR^1R^2$, represent a 4- through 8-membered cyclic amino group optionally containing nitrogen, oxygen, or sulfur as a ring member in addition to said N atom and optionally being further substituted.

11. A method of treating rheumatoid arthritis in humans or animals which comprising administering to said humans or animals a therapeutically effective amount of a compound of the following formula (I) or a salt thereof, or a solvate thereof,

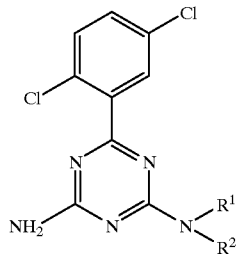

[1]

wherein $R^1$ represents hydrogen, optionally substituted alkyl, aralkyl, arylalkenyl, or aryl; $R^2$ represents optionally substituted alkyl, aralkyl, arylalkenyl, or aryl; or $R^1$ and $R^2$ conjoinedly and taken together with the adjacent N atom, i.e. in the form of $NR^1R^2$, represent a 4- through 8-membered cyclic amino group optionally containing nitrogen, oxygen, or sulfur as a ring member in addition to said N atom and optionally being further substituted.

12. The method according to claim 1, comprising administering a pharmaceutical composition comprising a compound of the formula (I) or a salt thereof, or a solvate thereof and a pharmaceutically acceptable nontoxic carrier or vehicle.

13. The method according to claim 12, wherein the administration is oral, parenteral or rectal.

14. The method according to claim 8, comprising administering a pharmaceutical composition comprising a compound of the formula (I) or a salt thereof, or a solvate thereof and a pharmaceutically acceptable nontoxic carrier or vehicle.

15. The method according to claim 14 wherein the administration is oral, parenteral or rectal.

16. The method according to claim 9, comprising administering a pharmaceutical composition comprising a compound of the formula (I) or a salt thereof, or a solvate thereof and a pharmaceutically acceptable nontoxic carrier or vehicle.

17. The method according to claim 16, wherein the administration is oral, parenteral or rectal.

18. The method according to claim 10, comprising administering a pharmaceutical composition comprising a compound of the formula (I) or a salt thereof, or a solvate thereof and a pharmaceutically acceptable nontoxic carrier or vehicle.

19. The method according to claim 18, wherein the administration is oral, parenteral or rectal.

20. The method according to claim 11, comprising administering a pharmaceutical composition comprising a compound of the formula (I) or a salt thereof, or a solvate thereof and a pharmaceutically acceptable nontoxic carrier or vehicle.

21. The method according to claim 20, wherein the administration is oral, parenteral or rectal.

* * * * *